(12) United States Patent
Park et al.

(10) Patent No.: US 12,010,770 B2
(45) Date of Patent: Jun. 11, 2024

(54) ELECTRONIC DEVICE AND OPERATING METHOD OF ELECTRONIC DEVICE

(71) Applicant: SAMSUNG ELECTRONICS CO., LTD., Suwon-si (KR)

(72) Inventors: Jeongho Park, Seoul (KR); Raeyoung Kim, Suwon-si (KR); Juhwa Kim, Hwaseong-si (KR); Long Yan, Hwaseong-si (KR); Sungjin Jung, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 227 days.

(21) Appl. No.: 17/474,834

(22) Filed: Sep. 14, 2021

(65) Prior Publication Data

US 2022/0191981 A1   Jun. 16, 2022

(30) Foreign Application Priority Data

Dec. 16, 2020   (KR) .................. 10-2020-0176795

(51) Int. Cl.
*H05B 45/12* (2020.01)
*A61B 5/00* (2006.01)
(Continued)

(52) U.S. Cl.
CPC ......... *H05B 45/12* (2020.01); *A61B 5/02416* (2013.01); *A61B 5/7225* (2013.01);
(Continued)

(58) Field of Classification Search
CPC ..... H05B 45/12; H05B 47/11; A61B 5/02416; A61B 5/7225; A61B 5/024; A61B 5/145;
(Continued)

(56) References Cited

U.S. PATENT DOCUMENTS 6,812,466 B2   11/2004   O'Connor et al.
8,097,853 B2    1/2012   Ji et al.
(Continued)

FOREIGN PATENT DOCUMENTS

KR   10-1241676   3/2013
KR   10-1645571   8/2016

OTHER PUBLICATIONS

Jongpak Kim et al., "Low-Power Photoplethysmogram Acquisition Integrated Circuit with Robust Light Interference Compensation", Sensors 2016.
(Continued)

*Primary Examiner* — Eric F Winakur
*Assistant Examiner* — Abid A Mustansir
(74) *Attorney, Agent, or Firm* — F. Chau & Associates, LLC

(57) ABSTRACT

An electronic device includes a light source, a light sensor, and a controller that senses an amount of a coarse ambient light by turning off the light source and performing sensing in a coarse mode by using the light sensor and senses an amount of a fine ambient light by performing sensing in a fine mode by using the light sensor. The controller senses an amount of a target light by turning on the light source and performing sensing by using the light sensor while the light source emits a light, and outputs information based on the amount of the coarse ambient light, the amount of the fine ambient light, and the amount of the target light.

20 Claims, 15 Drawing Sheets

(51) Int. Cl.
*A61B 5/024* (2006.01)
*A61B 5/145* (2006.01)
*A61B 5/1455* (2006.01)
*H05B 47/11* (2020.01)

(52) U.S. Cl.
CPC .............. *A61B 5/024* (2013.01); *A61B 5/145* (2013.01); *A61B 5/14552* (2013.01); *A61B 5/7203* (2013.01); *A61B 2560/0247* (2013.01); *H05B 47/11* (2020.01)

(58) Field of Classification Search
CPC .............. A61B 5/14552; A61B 5/7203; A61B 2560/0247; A61B 5/02427; A61B 5/725; G06F 3/011; G06F 2218/00; G16Y 20/40; G16Y 40/10
See application file for complete search history.

(56) References Cited

U.S. PATENT DOCUMENTS

| | | | |
|---|---|---|---|
| 10,362,994 | B2 | 7/2019 | Ahmed et al. |
| 10,512,407 | B2 | 12/2019 | Richards et al. |
| 10,736,575 | B2 | 8/2020 | Gunturi et al. |
| 2009/0121889 | A1 | 5/2009 | Lin et al. |
| 2017/0245803 | A1* | 8/2017 | Ahmed ............... A61B 5/7203 |

OTHER PUBLICATIONS

Best-in-Class Optical Pulse Oximeter and Heart-Rate Sensor AFE for Wearable Health; https://www.maximintegrated.com/en/products/sensors/MAX86 170B.html; Apr. 27, 2021.

\* cited by examiner

ELECTRONIC DEVICE AND OPERATING METHOD OF ELECTRONIC DEVICE

CROSS-REFERENCE TO RELATED APPLICATIONS

This U.S. non-provisional patent application claims priority under 35 U.S.C. § 119 to Korean Patent Application No. 10-2020-0176795 filed on Dec. 16, 2020, in the Korean Intellectual Property Office, the disclosure of which is incorporated by reference in its entirety herein.

1. TECHNICAL FIELD

Embodiments of the present disclosure described herein relate to an electronic device, and more particularly, relate to an electronic device for performing photoplethysmography and an operating method of the electronic device.

2. DISCUSSION OF RELATED ART

As technologies for manufacturing a mobile device or a wearable device develop, various applications may be implemented at the mobile device or the wearable device. For example, photoplethysmography may be performed by the mobile device or the wearable device.

Photoplethysmography is an optical technique for sensing contraction and expansion of blood vessels of a user. The technique includes emitting a light to blood vessels and sensing an amount of the light penetrating the blood vessels or an amount of the light reflected from the blood vessels and using the sensed amount to determine a pulse. The photoplethysmography may be implemented at a mobile device or a wearable device since they may be in continuous contact with a user. Thus, devices such as a smart watch, smart glasses, an earphone, or a smartphone can be used to provide health information to a user.

SUMMARY

At least one embodiment of the present disclosure provides an electronic device for performing photoplethysmography with an improved speed and with improved accuracy and an operating method of the electronic device.

According to an embodiment, an electronic device includes a light source, a light sensor, and a controller that senses an amount of a coarse ambient light by turning off the light source and performing sensing in a coarse mode by using the light sensor and senses an amount of a fine ambient light by performing sensing in a fine mode by using the light sensor. The controller senses an amount of a target light by turning on the light source and performing sensing by using the light sensor while the light source emits a light, and outputs information based on the amount of the coarse ambient light, the amount of the fine ambient light, and the amount of the target light.

According to an embodiment, an operating method of an electronic device which includes a light source and a light sensor includes sensing a turning off the light source and first current amount by using the light sensor during a first time interval, canceling a current corresponding to the first current amount from an output of the light sensor during a second time interval and a third time interval, sensing a second current amount by using the light sensor during the second time interval, and during the third time interval, emitting a light by turning on the light source and sensing a third current amount by using the light sensor.

According to an embodiment, an electronic device includes a photoplethysmography device that outputs a photoplethysmography signal, and a processor that receives the photoplethysmography signal from the photoplethysmography device and communicates the photoplethysmography signal to an external device. The photoplethysmography device includes a light source, a light sensor, and a controller configured to perform sensing by turning off the light source and using the light sensor to sense an amount of a coarse ambient light, in a coarse mode. During canceling a current corresponding to the amount of the coarse ambient light from an output of the light sensor, the controller senses an amount of a fine ambient light by performing sensing by using the light sensor in a fine mode, and senses an amount of a target light by performing turning on the light source and sensing by using the light sensor while the light source emits a light.

According to an exemplary embodiment, a device for performing photoplethysmography includes a light source, a light sensor, an ADC, and a controller. The controller is configured to turn off the light source, control the light sensor to output a first signal representing first ambient light, and control the ADC to convert the first signal into a second signal having a first number of bits. The controller is further configured to control the light sensor to output a third signal representing second ambient light, subtract the second signal from the third signal to generate a fourth signal, and control the ADC to convert the fourth signal into a fifth signal having a second number of bits greater than the first number. The controller is additionally configured to configured turn on the light source, control the light sensor to output a sixth signal representing a target light, and subtract the fifth signal from the sixth signal to generate a photoplethysmography signal.

BRIEF DESCRIPTION OF THE FIGURES

The present disclosure will become apparent by describing in detail embodiments thereof with reference to the accompanying drawings.

DETAILED DESCRIPTION OF THE EMBODIMENTS

Below, embodiments of the present disclosure are described in detail and clearly to such an extent that one of ordinary skill in the art may implement the present disclosure.

Figure 1:
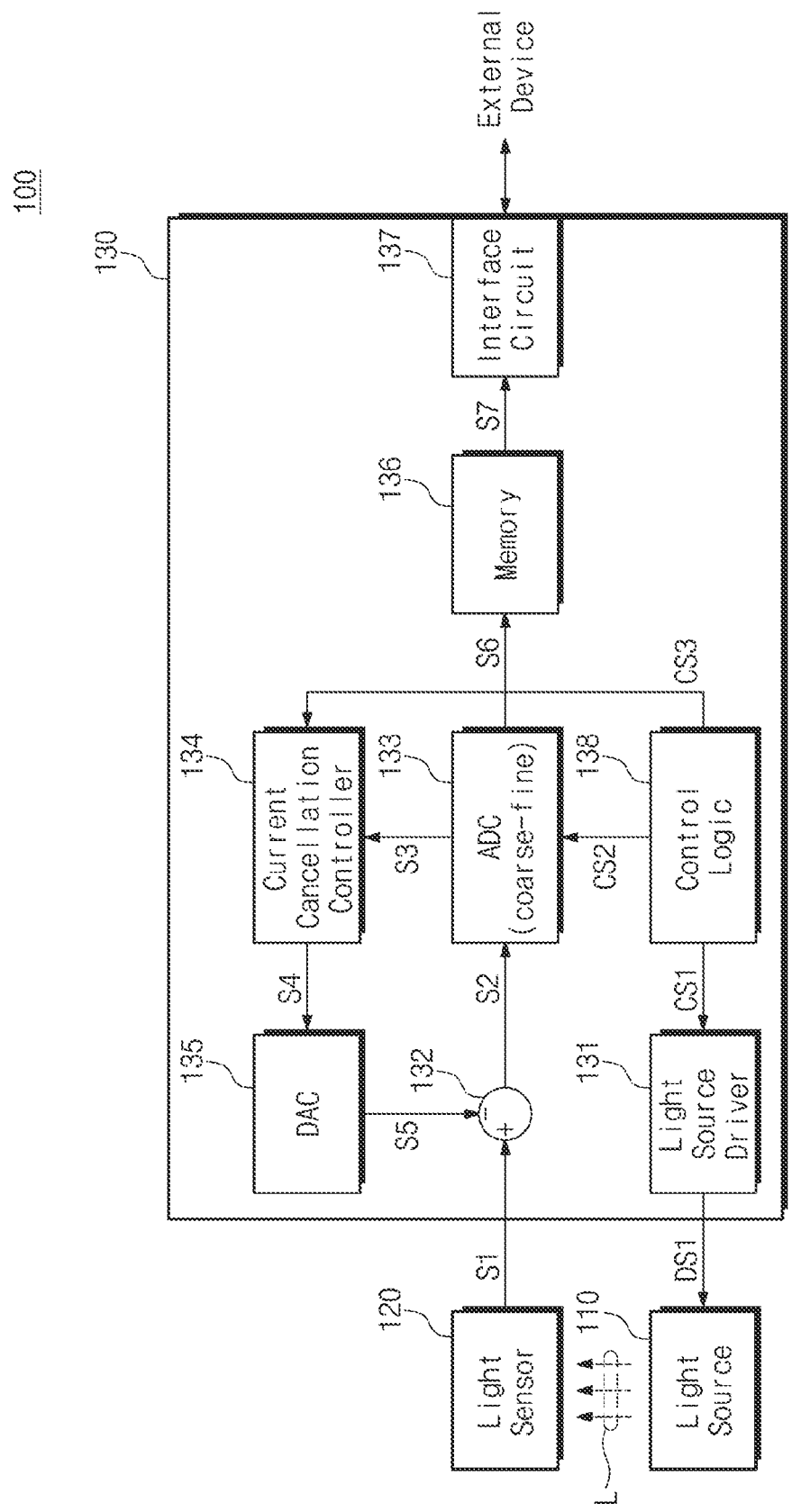
FIG. 1 illustrates an electronic device according to an exemplary embodiment of the present disclosure.

FIG. 1 illustrates an electronic device 100 according to an exemplary embodiment of the present disclosure. Referring to FIG. 1, the electronic device 100 includes a light source 110, a light sensor 120, and a controller 130 (e.g., a control circuit).

The light source 110 may be controlled by a first driving signal DS1 of the controller 130. The light source 110 may emit a light "L" during a time period that is controlled by the first driving signal DS1. For example, the light source 110 may include a light-emitting diode (LED).

The light sensor 120 may output a first signal S1 based on an incident light. The incident light may be provided by the light source 110. For example, the light sensor 120 may include a photodiode. The light sensor 120 may output the first signal S1 in the form of a current. For example, the light sensor 120 is illustrated in FIG. 1 as a current source that outputs a current corresponding to the amount of incident light, but the light sensor 120 may be implemented with a current sink that sinks a current corresponding to the amount of incident light.

The controller 130 may turn on or turn off the light source 110 using the first driving signal DS1. For example, the first driving signal DS1 could be set to a first logical state to indicate that the light source 110 is to be turned on and set to a second other logical state to indicate that the light source 110 is to be turned off. When the light source 110 is turned on, the light source 110 emits the light "L". When the light source 110 is turned off, the light source 110 stops emitting the light "L". The controller 130 may receive the first signal S1 from the light sensor 120.

In an embodiment, the controller 130 includes a light source driver 131 (e.g., a driver circuit), a subtractor 132 (e.g., an arithmetic logic circuit), an analog-to-digital converter (ADC) 133, a current cancellation controller 134 (e.g., a control circuit), a digital-to-analog converter (DAC) 135, a memory 136, an interface circuit 137, and control logic 138 (e.g., a logic circuit).

The light source driver 131 may generate the first driving signal DS1 in response to a first control signal CS1 received from the control logic 138. The light source driver 131 may turn on or turn off the light source 110 based on the first driving signal DS1.

In an embodiment, the subtractor 132 subtracts a fifth signal S5 (e.g., a current or a current amount) transferred from the digital-to-analog converter 135 from the first signal S1 (e.g., a current or a current amount) received from the light source 110. The subtractor 132 may output a result of the subtraction as a second signal S2 (e.g., a current or a current amount). For example, the subtractor 132 may be implemented in the form of a wire connection that does not require a separate circuit.

The analog-to-digital converter (ADC) 133 may receive the second signal S2 from the subtractor 132. The ADC 133 may operate in response to a second control signal CS2 received from the control logic 138. For example, the ADC 133 may operate in a coarse mode or a fine mode.

In the coarse mode, the ADC 133 converts the second signal S2 into a first digital value and outputs the first digital value as a third signal S3. In the fine mode, the ADC 133 converts the second signal S2 into a second digital value or a third digital value and outputs the second digital value or the third digital value as a sixth signal S6.

For example, the number of bits of the third signal S3 output from the ADC 133 in the coarse mode may be different from the number of bits of the sixth signal S6 output from the ADC 133 in the fine mode. For example, the third signal S3 may be a 10-bit signal, and the sixth signal S6 may be a 24-bit signal. In an embodiment, the number of bits of the third signal S3 is less than the number of bits of the sixth signal S6.

The current cancellation controller 134 may receive the third signal S3 from the ADC 133. The current cancellation controller 134 may operate in response to a third control signal CS3 received from the control logic 138. The current cancellation controller 134 converts the third signal S3 into a fourth signal S4.

For example, the third signal S3 may include bits, the number of which corresponds to a resolution of the coarse mode of the ADC 133. The fourth signal S4 may include bits, the number of which corresponds to a resolution of the digital-to-analog converter (DAC) 135. For example, the third signal S3 may be a 10-bit signal, and the fourth signal S4 may be an 8-bit signal. In an embodiment, the number of bits of the fourth signal S4 is less than the number of bits of the third signal S3.

The current cancellation controller 134 may receive a gain and an offset from the control logic 138. The current cancellation controller 134 may convert the third signal S3 into the fourth signal S4, based on the gain and the offset received from the control logic 138.

The DAC 135 may receive the fourth signal S4 from the current cancellation controller 134. The DAC 135 converts the fourth signal S4 into the fifth signal S5. The fifth signal S5 may be a current, the amount of which corresponds to a value of bits of the fourth signal S4. For example, a value of the current of the fifth signal may indicate a value of the bits of the fourth signal S4.

The memory 136 may store a second digital value and a third digital value output from the ADC 133 as the sixth signal S6 in the fine mode. Logic that calculates a difference between the second digital value and the third digital value stored in the memory 136 may be included in the control logic 138 or in the controller 130 as a component coupled such that communication with the memory 136 is possible. The memory 136 may output the second digital value, the third digital value, or the calculated difference to the interface circuit 137 as a seventh signal S7.

The interface circuit 137 may output information including the second digital value, the third digital value, or the calculated difference to an external device. In an embodiment, the output information is a photoplethysmography signal. The photoplethysmography signal may be used to detect volumetric changes in blood in peripheral circulation. In an embodiment, a value or amplitude of the photoplethysmography signal is proportional to the quantity of blood flowing through the blood vessels. The photoplethysmography signal may include several components that indicate volumetric changes in arterial blood associated with cardiac activity, variations in venous blood volume that modules the photoplethysmography signal, and a direct current (DC) component indicating an optical property of tissue and subtle energy changes in the body. Further, the pulse of a user may be determined from the photoplethysmography signal.

Alternatively, the interface circuit 137 may transfer control information, mode information, or a command transferred from the external device to the control logic 138

Figure 2:
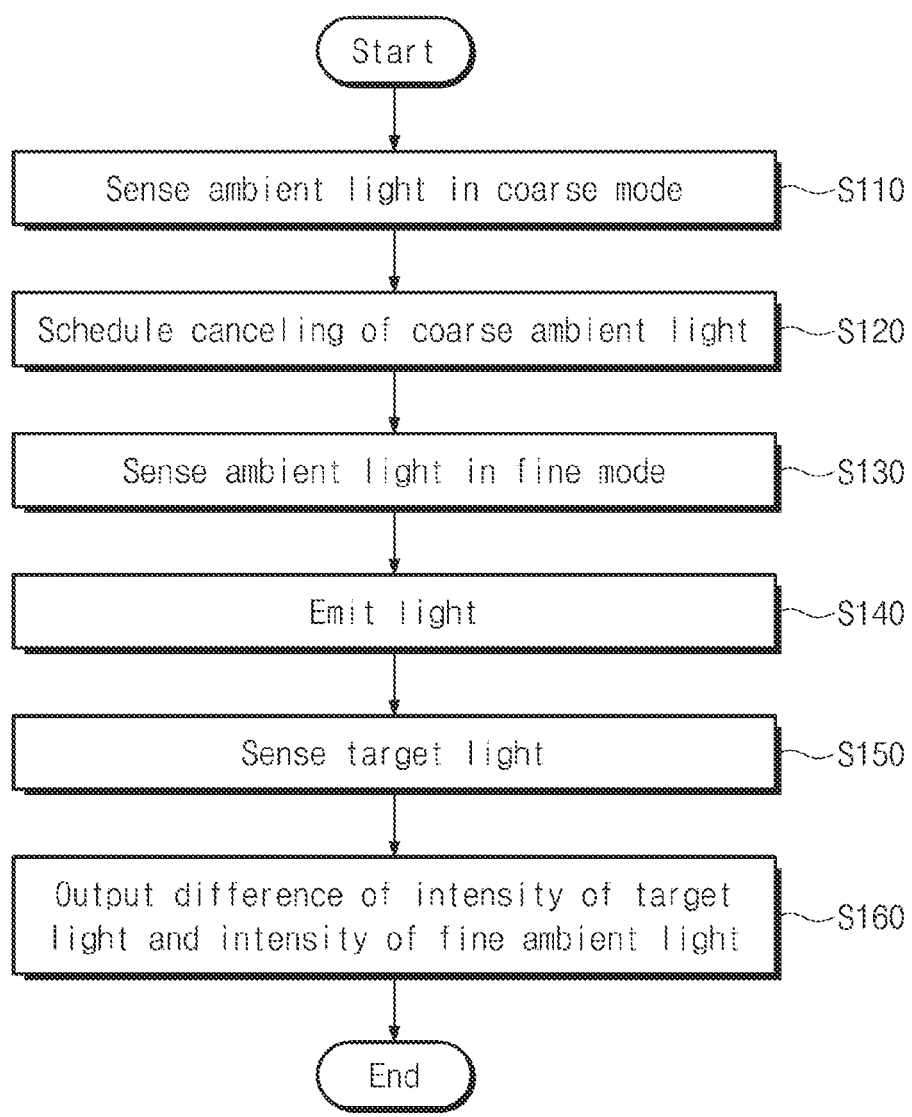
FIG. 2 illustrates an operating method of an electronic device according to an exemplary embodiment of the present disclosure.

FIG. 2 illustrates an operating method of the electronic device 100 according to an embodiment of the present disclosure. Referring to FIGS. 1 and 2, in operation S110, the electronic device 100 senses an ambient light in the coarse mode. For example, the electronic device 100 does not turn on the light source 110 and senses an incident light by using the light sensor 120. Because the light source 110 is in a turn-off state, the light sensed by the light sensor 120 may be an ambient light.

The controller 130 may sense the incident ambient light in the coarse mode. For example, in the coarse mode, based on an incident light, the ADC 133 may convert a current (or a current amount), which the light sensor 120 generates, into a first digital value with lower accuracy than in the fine mode and at a higher speed than in the fine mode. For example, a coarse ambient light may be an ambient light (or a current), which the electronic device 100 senses in the coarse mode, or the intensity of the ambient light (or a current amount).

In operation S120, the electronic device 100 schedules the coarse ambient light to be canceled or removed from the ambient light. For example, the current cancellation controller 134 may apply the fourth signal S4 to the DAC 135 so that the DAC 135 applies a fifth signal S5 to the subtractor 132 at a same time when a first signal S1 representing next ambient light is also applied to the subtractor 132. For example, a coarse ambient light may be an ambient light (or a current), which the electronic device 100 senses in the coarse mode, or the intensity of the ambient light (or a current amount). The current cancellation controller 134 of the controller 130 may control the DAC 135 through the fourth signal S4 so as to generate a current (e.g., the fifth signal S5) corresponding to the coarse ambient light.

In operation S130, the electronic device 100 senses an ambient light in the fine mode. For example, the electronic device 100 does not turn on the light source 110 and senses an incident light by using the light sensor 120. Because the light source 110 is in a turn-off state, the light sensed by the light sensor 120 may be an ambient light. In an embodiment, while the electronic device 100 is sensing ambient light and applying the first signal S1 representing the sensed ambient light to an input of subtractor 132, the DAC 135 is applying the fifth signal S5 representing the coarse ambient light to another input of the subtractor 132 so that the coarse ambient light can be subtracted from the sensed ambient light to generate adjusted ambient light that is applied to the ADC 133 in the fine mode to sense fine ambient light.

The controller 130 may sense the incident ambient light in the fine mode. For example, in the fine mode, based on an incident light, the ADC 133 may convert a current (or a current amount), which the light sensor 120 generates, into a second digital value with higher accuracy than in the coarse mode and at a lower speed than in the coarse mode. The ADC 133 may store the second digital value in the memory 136 as an intensity of fine ambient light.

In operation S140, the electronic device 100 emits the light "L" by using the light source 110. The control logic 138 of the controller 130 controls the light source driver 131 through the first control signal CS1. In response to the first control signal CS1, the light source driver 131 generate the first driving signal DS1 and turns on the light source 110 by using the first driving signal DS1. When turned on, the light source 110 may emit the light "L".

In operation S150, while the light source 110 emits the light "L", the electronic device 100 senses an incident light as a target light by using the light sensor 120. The target light may represent a light corresponding to a sum of an ambient light and a light penetrating a part of a body of the user or reflected from the part of the body of the user after the light "L" is emitted thereto.

In an embodiment, the controller 130 senses the incident target light in the fine mode. For example, in the fine mode, based on the target light, the ADC 133 may convert a current (or a current amount), which the light sensor 120 generates, into a third digital value with higher accuracy than in the coarse mode and at a lower speed than in the coarse mode. The ADC 133 may store the third digital value in the memory 136.

In operation S160, the electronic device 100 outputs a difference between the intensity of the target light and the intensity of the fine ambient light sensed in the fine mode. For example, the memory 136 may output a difference between the third digital value and the second digital value to the external device through the interface circuit 137.

As described above, the coarse ambient light measured at a relatively high speed is canceled by subtracting the fifth signal S5 corresponding to the intensity of the coarse ambient light from the first signal S1 corresponding to the intensity of the ambient light output from the light sensor 120. Afterwards, a fine ambient light and a target light are sensed in the fine mode. Because a component of a coarse ambient light is canceled from an incident light, the ADC 133 may convert a fine ambient light and a target light more quickly and more accurately.

Figure 3:
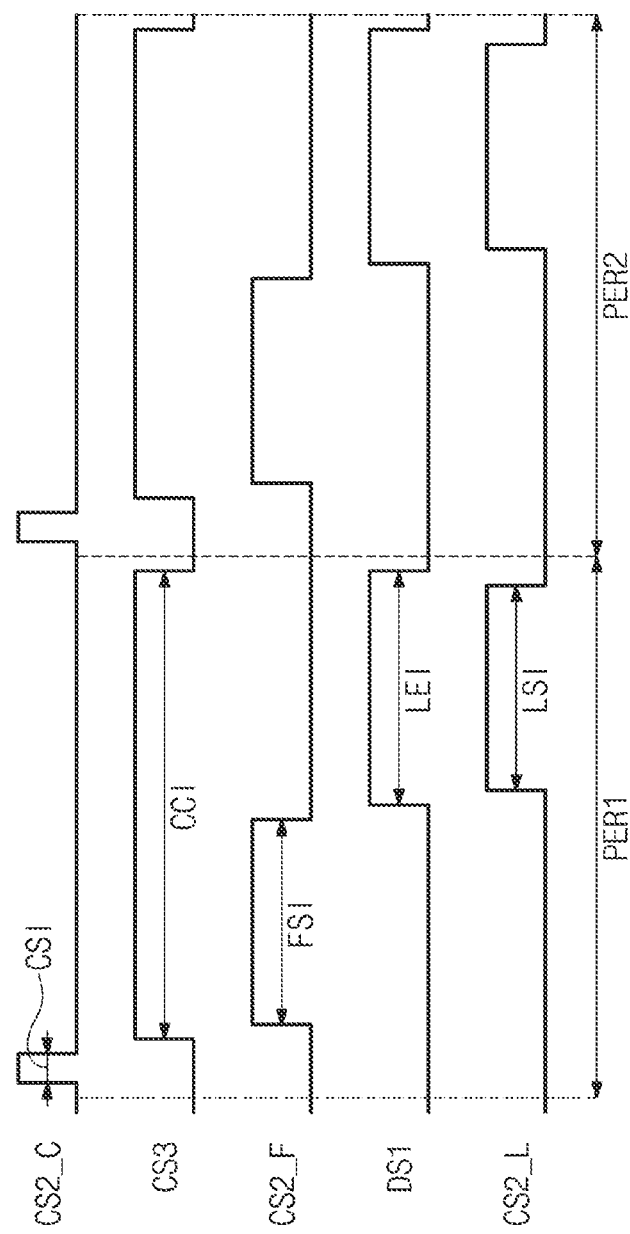
FIG. 3 illustrates a first example of waveforms of signals when an electronic device operates.

FIG. 3 illustrates an example of waveforms of signals when the electronic device 100 operates. Referring to FIGS. 1 and 3, the electronic device 100 may operate based on a specific period, that is, periodically. A first period PER1 and a second period PER2 of the electronic device 100 are illustrated in FIG. 3 by way of example. Each of the first period PER1 and the second period PER2 may include a first interval, a second interval, and a third interval.

The first interval may include a coarse sensing interval CSI. In the coarse sensing interval CSI, the control logic 138 may activate a second coarse control signal CS2_C. The second coarse control signal CS2_C may be included in the second control signal CS2. In response to the second coarse control signal CS2_C, the ADC 133 may convert the second signal S2 into a first digital value in the coarse mode. The second signal S2 may be a current (or a current amount) corresponding to the intensity of ambient light. The ADC 133 may transfer the first digital value to the current cancellation controller 134 as the third signal S3.

The current cancellation controller 134 may generate the fourth signal S4 by converting (or without converting) the third signal S3. The second interval and the third interval may be included in a current cancellation interval CCI. During the current cancellation interval CCI, the DAC 135 may transfer a current corresponding to a coarse ambient light to the subtractor 132 as the fifth signal S5.

The second interval may include a fine sensing interval FSI. During the fine sensing interval FSI, the control logic 138 may activate a second fine control signal CS2_F. The second fine control signal CS2_F may be included in the second control signal CS2. In response to the second fine control signal CS2_F, the ADC 133 may convert the second signal S2 into a second digital value in the fine mode. During the fine sensing interval FSI, the second signal S2 may be a current (or a current amount) corresponding to the intensity of fine ambient light that is obtained by subtracting the intensity of coarse ambient light from the intensity of ambient light. The ADC 133 may transfer the second digital value to the memory 136 as the sixth signal S6.

The third interval may include a light-emitting interval LEI and a target light sensing interval LSI. During the light-emitting interval LEI, the control logic 138 may activate the first driving signal DS1 through the first control signal CS1. During the light-emitting interval LEI, the light source 110 may emit the light "L". In an embodiment, the light source 110 emits infrared light.

The target light sensing interval LSI may coincide with the light-emitting interval LEI or may be included in the light-emitting interval LEI. During the target light sensing interval LSI, the control logic 138 may activate a second target light sensing control signal CS2_L. In response to the second target light sensing control signal CS2_L, the ADC 133 may convert the second signal S2 into a third digital value in the fine mode. During the target light sensing interval LSI, the second signal S2 may be a current (or a current amount) corresponding to a portion of the light "L", which is incident onto the light sensor 120, and the intensity of fine ambient light obtained by subtracting the intensity of coarse ambient light from the intensity of ambient light. The ADC 133 may transfer the third digital value to the memory 136 as the sixth signal S6.

During the second period PER2, signals may be controlled identically as in the first period PER1. In each period, the memory 136 may output a difference between the third digital value and the second digital value to the interface circuit 137 as the seventh signal S7. In each period, the memory 136 may output the second digital value or the third digital value to the interface circuit 137 as the seventh signal S7.

When a debug mode is set by the control logic 138, in each period, the ADC 133 may transfer a first digital value to the memory 136. In each period, the memory 136 may output the first digital value to the interface circuit 137 as the seventh signal S7. The interface circuit 137 may output information, which is included in the seventh signal S7 received from the memory 136 in each period, to the external device. After each period elapses, the first digital value, the second digital value, or the third digital value may be initialized (or reset).

Figure 4:
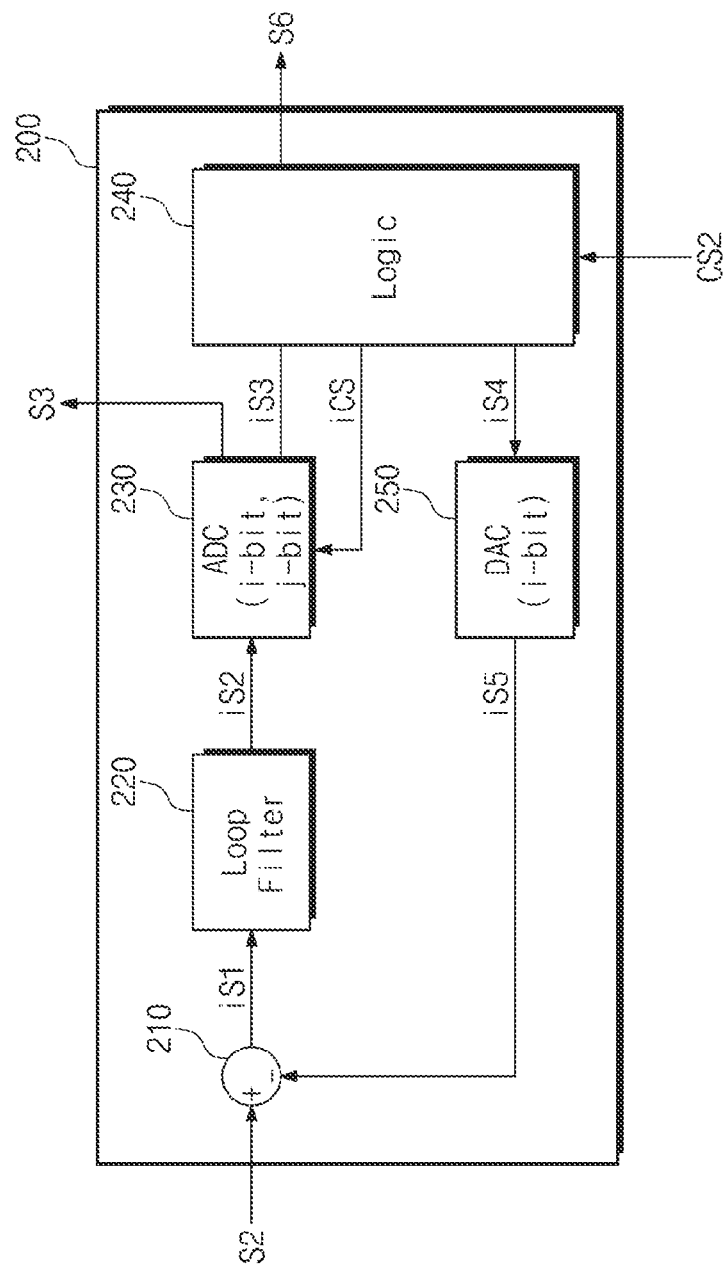
FIG. 4 illustrates an analog-to-digital converter according to an exemplary embodiment of the present disclosure.

FIG. 4 illustrates an ADC 200 according to an exemplary embodiment of the present disclosure. For example, the ADC 200 may correspond to the ADC 133 of FIG. 1. Referring to FIGS. 1 and 4, the ADC 200 includes an internal subtractor 210, a loop filter 220, an internal ADC 230, logic 240 (e.g., a logic circuit), and an internal DAC 250.

The internal subtractor 210 may receive the second signal S2 from the subtractor 132. The internal subtractor 210 may receive a fifth internal signal iS5 from the internal DAC 250. The internal subtractor 210 may output a result of subtracting the fifth internal signal iS5 (or a current or a current amount) from the second signal S2 (e.g., a current or a current amount), as a first internal signal iS1. For example, the internal subtractor 210 may be implemented in the form of a wire connection.

The loop filter 220 may filter the first internal signal iS1 to output a second internal signal iS2. For example, the loop filter 220 may include a three-order loop filter.

The internal ADC 230 may receive the second internal signal iS2 from the loop filter 220. The internal ADC 230 may operate in the coarse mode and the fine mode. In the coarse mode, the internal ADC 230 may convert the second internal signal iS2 into a first digital value of "j" bits. The internal ADC 230 may transfer the first digital value as the third signal S3. In an embodiment, the number of "j" bits may be 10.

In the fine mode, the internal ADC 230 may convert the second internal signal iS2 into an i-bit value. The internal ADC 230 may transfer the i-bit value to the logic 240 as a third internal signal iS3. In an embodiment, the number of "i" bits may be 5.

The logic 240 may operate in response to the second control signal CS2. The logic 240 may control the internal ADC 230 through an internal control signal iCS. In an embodiment, the logic 240 may control the internal ADC 230 in the coarse mode or the fine mode.

In the fine mode, the logic 240 may receive the third internal signal iS3 from the internal ADC 230. The logic 240 may provide the internal DAC 250 with the third internal signal iS3 as a fourth internal signal iS4. The logic 240 may perform filtering on the third internal signal iS3 to output the sixth signal S6. In the debug mode, the logic 240 may cause the internal ADC 230 to output the third signal S3 to the logic 240.

The internal DAC 250 may receive the fourth internal signal iS4 from the logic 240. The internal DAC 250 may generate a current corresponding to a value of the fourth internal signal iS4 to output the current as the fifth internal signal iS5. In an embodiment, the internal DAC 250 may function as a current source or a current sink.

In an embodiment, in the coarse mode, the logic 240 deactivates the internal DAC 250. In the coarse mode, the ADC 200 may convert the second signal S2 into the third signal S3 by using a successive-approximation (SAR) ADC as the internal ADC 230.

In an embodiment, in the fine mode, the logic 240 activates the internal DAC 250. In the fine mode, the ADC 200 may operate as a delta-sigma ADC that converts the second signal S2 into the sixth signal S6 by using the internal subtractor 210, the loop filter 220, the internal ADC 230, the logic 240, and the internal DAC 250.

Figure 5:
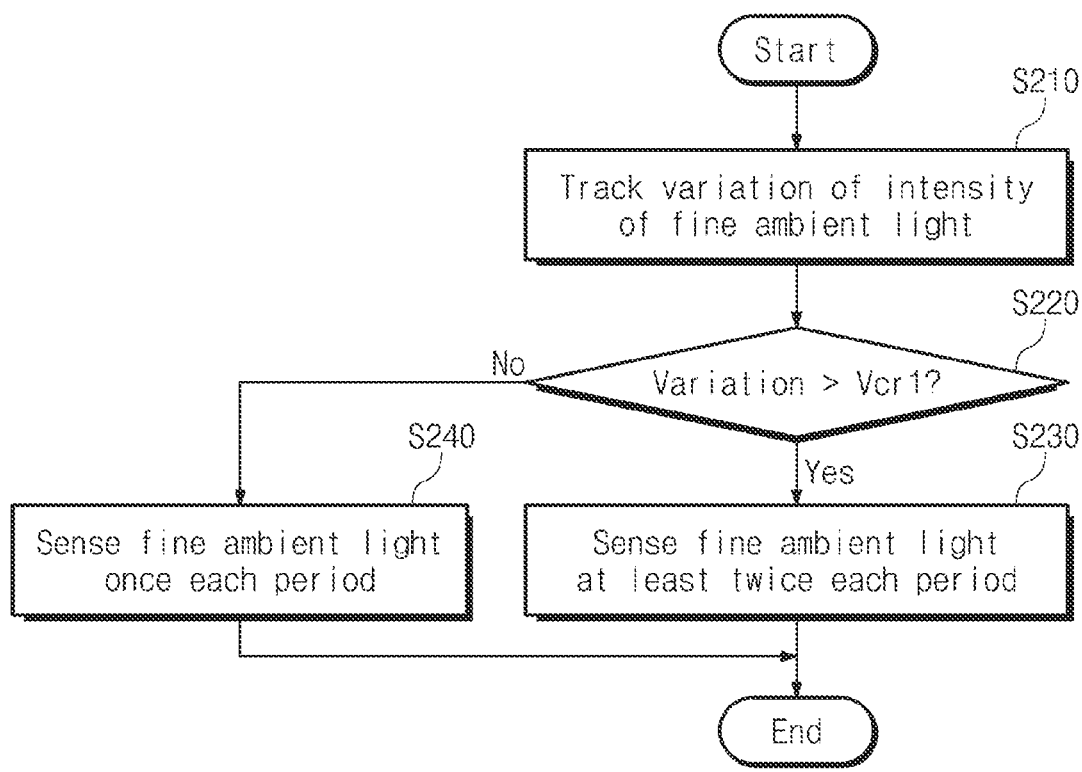
FIG. 5 illustrates a first example in which an electronic device adaptively operates.

FIG. 5 illustrates an example in which the electronic device 100 adaptively operates. Referring to FIGS. 1 and 5, in operation S210, the control logic 138 of the electronic device 100 may receive information about the intensity of fine ambient light, that is, a second digital value from the ADC 133. The control logic 138 may track the variation of the intensity of fine ambient light, based on a change of the second digital value. For example, the control logic 138 could internally save a prior intensity of the fine ambient light previously received from the ADC 133 and then subtract a new intensity of the fine ambient light next received from the ADC 133 to calculate a variation of the intensity of fine ambient light.

In operation S220, the control logic 138 determines whether the variation of the intensity of fine ambient light is greater than a first critical value Vcr1. For example, the control logic 138 may determine whether the variation of the intensity of fine ambient light during a given number of continuous periods is greater than the first critical value Vcr1. When the variation of the intensity of fine ambient light is greater than the first critical value Vcr1, in operation S230, the control logic 138 of the electronic device 100 controls the controller 130 such that a fine ambient light is sensed at least twice in each period.

When the variation of the intensity of fine ambient light is not greater than the first critical value Vcr1, in operation S240, the control logic 138 of the electronic device 100 controls the controller 130 such that a fine ambient light is sensed once in each period. When sensing a fine ambient light once in each period, the controller 130 may control signals based on the waveforms illustrated in FIG. 3.

In an embodiment, in response to a signal received from the external device through the interface circuit 137, the control logic 138 may control the controller 130 such that a fine ambient light is sensed once or at least twice in each period.

Figure 6:
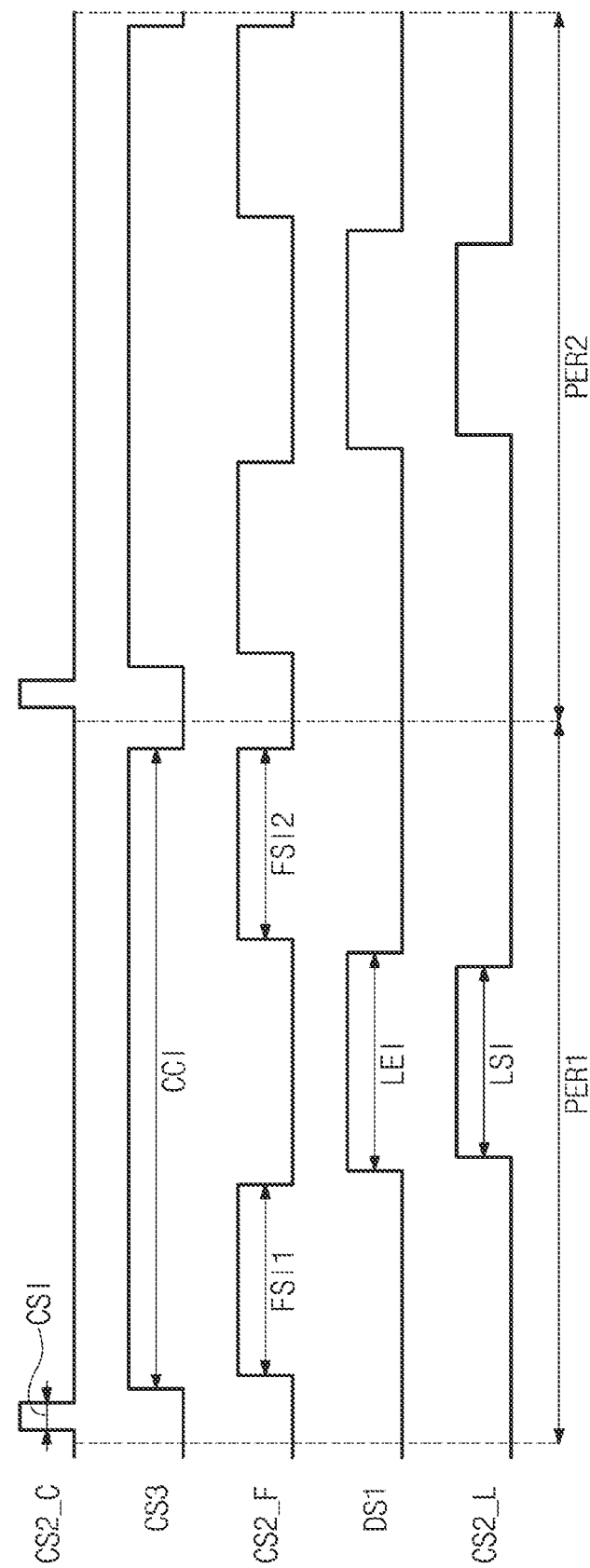
FIG. 6 illustrates an example of waveforms of signals when a controller senses a fine ambient light at least twice.

FIG. 6 illustrates an example of waveforms of signals when the controller 130 senses a fine ambient light at least twice. Referring to FIGS. 1 and 6, each of the first period PER1 and the second period PER2 may include a first time interval, a second time interval, a third time interval, and a fourth time interval.

As described with reference to FIG. 3, the first time interval may include the coarse sensing interval CSI. Based on a first digital value sensed in the coarse sensing interval CSI, the controller 130 maintains the current cancellation interval CCI during the second time interval, the third time interval, and the fourth time interval.

As in the above description given with reference to FIG. 3, the second time interval may include a first fine sensing interval FSI1. The ADC 133 may store a second digital value converted from the second signal S2 during the first fine sensing interval FSI1 in the memory 136.

As described with reference to FIG. 3, the third time interval may include the light-emitting interval LEI and the target light sensing interval LSI. The ADC 133 may store a third digital value converted from the second signal S2 during the target light sensing interval LSI in the memory 136.

The fourth time interval may include a second fine sensing interval FSI2. As in the first fine sensing interval FSI1, the second fine sensing interval FSI2 is performed in a state where the light source 110 is turned off. The ADC 133 may store a fourth digital value converted from the second signal S2 during the second fine sensing interval FSI2 in the memory 136.

In each period, the memory 136 may calculate an average of the second digital value sensed in the first fine sensing interval FSI1 and the fourth digital value sensed in the second fine sensing interval FSI2 as a value of a fine ambient light. In an embodiment, logic that calculates an average of the second digital value and the fourth digital value stored in the memory 136 may be included in the control logic 138 or in the controller 130 as a component coupled such that communication with the memory 136 is possible. For example, the controller 130 or more specifically the control logic 138 could calculate the average.

An operation according to waveforms of signals of FIG. 6 is the same as the operation according to the waveforms of the signals of FIG. 3 except that an average value of the second digital value and the fourth digital value is used as a digital value of a fine ambient light. Thus, additional description will be omitted to avoid redundancy.

In an embodiment, a time length of the first fine sensing interval FSI1 is the same as a time length of the second fine sensing interval FSI2. In an embodiment, the controller 130 successively performs the first fine sensing interval FSI1 and the second fine sensing interval FSI2 and then performs the light-emitting interval LEI and the target light sensing interval LSI.

Alternatively, the controller 130 performs the light-emitting interval LEI and the target light sensing interval LSI and then successively performs the first fine sensing interval FSI1 and the second fine sensing interval FSI2. In an embodiment, based on the variation of the fine ambient light, the controller 130 may perform the fine sensing interval FSI three times or more in each period and may use an average of digital values sensed in the three or more fine light sensing intervals FSI, as a digital value of a fine ambient light.

Figure 7:
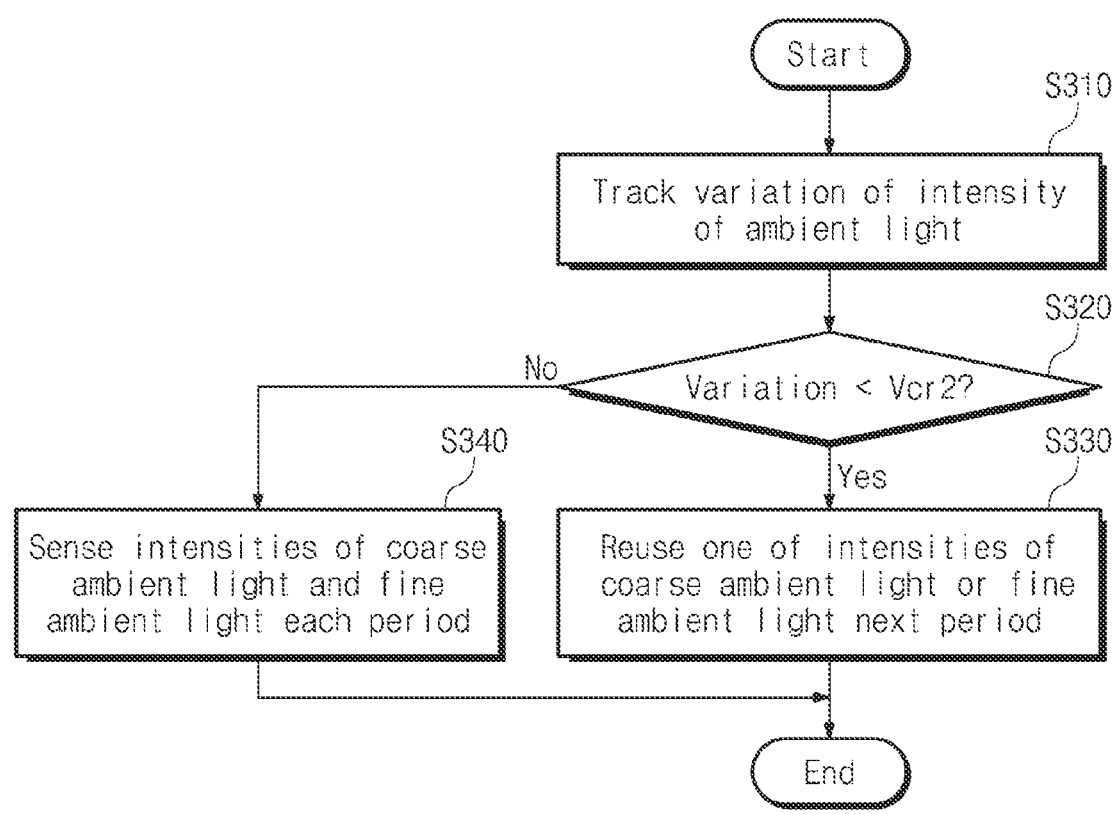
FIG. 7 illustrates a second example in which an electronic device adaptively operates.

FIG. 7 illustrates an example in which the electronic device 100 adaptively operates. Referring to FIGS. 1 and 7, in operation S310, the control logic 138 of the electronic device 100 may receive information about the intensity of ambient light, that is, a first digital value or a second digital value from the ADC 133. The control logic 138 tracks the variation of the intensity of ambient light, for example, the intensity of coarse ambient light or fine ambient light, based on a change of the first digital value or the second digital value.

In operation S320, the control logic 138 determines whether the variation of the intensity of ambient light (e.g., coarse ambient light or fine ambient light) is smaller than a second critical value Vcr2. For example, the control logic 138 may determine whether the variation of the intensity of ambient light (e.g., coarse ambient light or fine ambient light) during a given number of continuous periods is smaller than the second critical value Vcr2. When the variation of the intensity of ambient light (e.g., coarse ambient light or fine ambient light) is smaller than the second critical value Vcr2, in operation S330, the control logic 138 of the electronic device 100 controls the controller 130 such that the intensity of coarse ambient light or the intensity of fine ambient light obtained in a current period, that is, the first digital value or the second digital value is reused in a next period. For example, if the second critical value Vcr2 is 4, the intensity of the fine ambient light is 5 during a first period, and the intensity of the fine ambient light 6 during a second period, since 6−5 is less than 4, a fine ambient light of 5 could be used instead of the fine ambient light of 6 during a next third period to calculate the next variation. For example, the variation might not be detected as being larger than the first critical value Vcr1 without this reuse if the variation in ambient light gets gradually larger.

When the variation of the intensity of ambient light is not smaller than the second critical value Vcr2, in operation S340, the control logic 138 of the electronic device 100 may control the controller 130 such that a coarse ambient light and a fine ambient light are sensed in each period. When sensing a coarse ambient light and a fine ambient light in each period, the controller 130 may control signals based on the waveforms illustrated in FIG. 3.

In an embodiment, in response to a signal received from the external device through the interface circuit 137, the control logic 138 may allow the controller 130 to reuse the intensity of coarse ambient light or the intensity of fine ambient light obtained in a current period, that is, the first digital value or the second digital value in a next period or to sense a coarse ambient light and a fine ambient light in each period.

Figure 8:
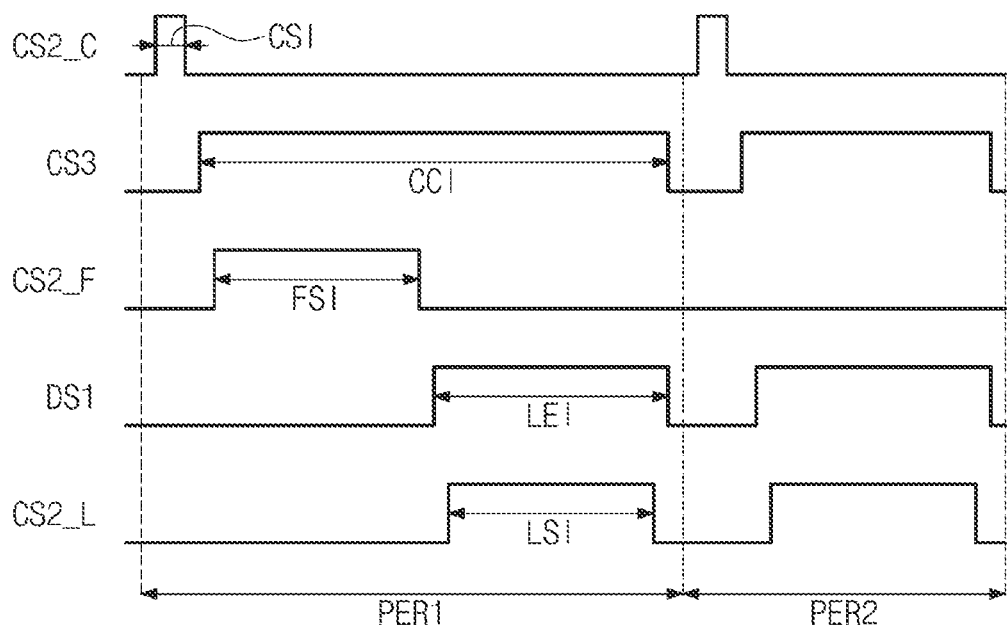
FIG. 8 illustrates an example of waveforms of signals when an electronic device reuses the intensity of fine ambient light, that is, a second digital value in a next period.

FIG. 8 illustrates an example of waveforms of signals when the electronic device 100 reuses the intensity of fine ambient light, that is, a second digital value in a next period.

Referring to FIGS. 1 and 8, the first period PER1 of FIG. 8 may be performed to be the same as the first period PER1 of FIG. 3.

The second period PER2 of FIG. 8 may be performed to be different from the second period PER2 of FIG. 3 or the second period PER2 of FIG. 8. In an embodiment, in the second period PER2 of FIG. 8, the second interval, that is, the fine sensing interval FSI is omitted. The control logic 138 may control the controller 130 such that the intensity of fine ambient light, that is, the second digital value stored in the memory 136 in the first period PER1 is reused in the second period PER2.

The electronic device 100 may reduce an operating time of a next period by reusing the intensity of fine ambient light, that is, the second digital value calculated in a current period in a next period. In an embodiment, the intensity of fine ambient light, that is, the second digital value corresponding to a specific period may be reused in two or more periods following the specific period. While the second digital value is reused, the second digital value may be maintained without initialization (or reset).

Figure 9:
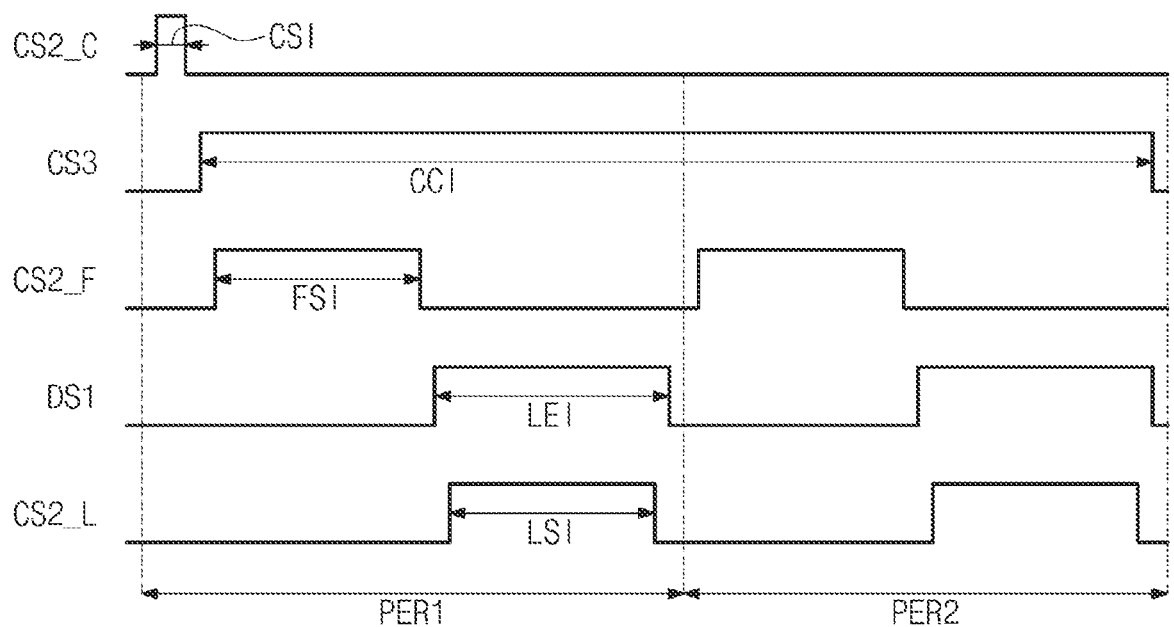
FIG. 9 illustrates an example of waveforms of signals when an electronic device reuses the intensity of coarse ambient light, that is, a first digital value in a next period.

FIG. 9 illustrates an example of waveforms of signals when the electronic device 100 reuses the intensity of coarse ambient light, that is, a first digital value in a next period. Referring to FIGS. 1 and 9, the first period PER1 of FIG. 9 may be performed to be the same as the first period PER1 of FIG. 3.

The second period PER2 of FIG. 9 may be performed to be different from the second period PER2 of FIG. 3 or the first period PER1 of FIG. 9. In an embodiment, in the second period PER2 of FIG. 9, the first interval, that is, the coarse sensing interval CSI is omitted. The control logic 138 may control the controller 130 such that the intensity of coarse ambient light, that is, the first digital value stored in the memory 136 in the first period PER1 is reused in the second period PER2.

The electronic device 100 may reduce an operating time of a next period by reusing the intensity of coarse ambient light, that is, the first digital value calculated in a current period in a next period. In an embodiment, the intensity of coarse ambient light, that is, the first digital value corresponding to a specific period may be reused in two or more periods following the specific period.

In an embodiment, when the first digital value corresponding to the intensity of coarse ambient light is reused, the current cancellation interval CCI may be maintained in the two or more periods. While the first digital value is reused, the first digital value may be maintained without initialization (or reset).

Figure 10:
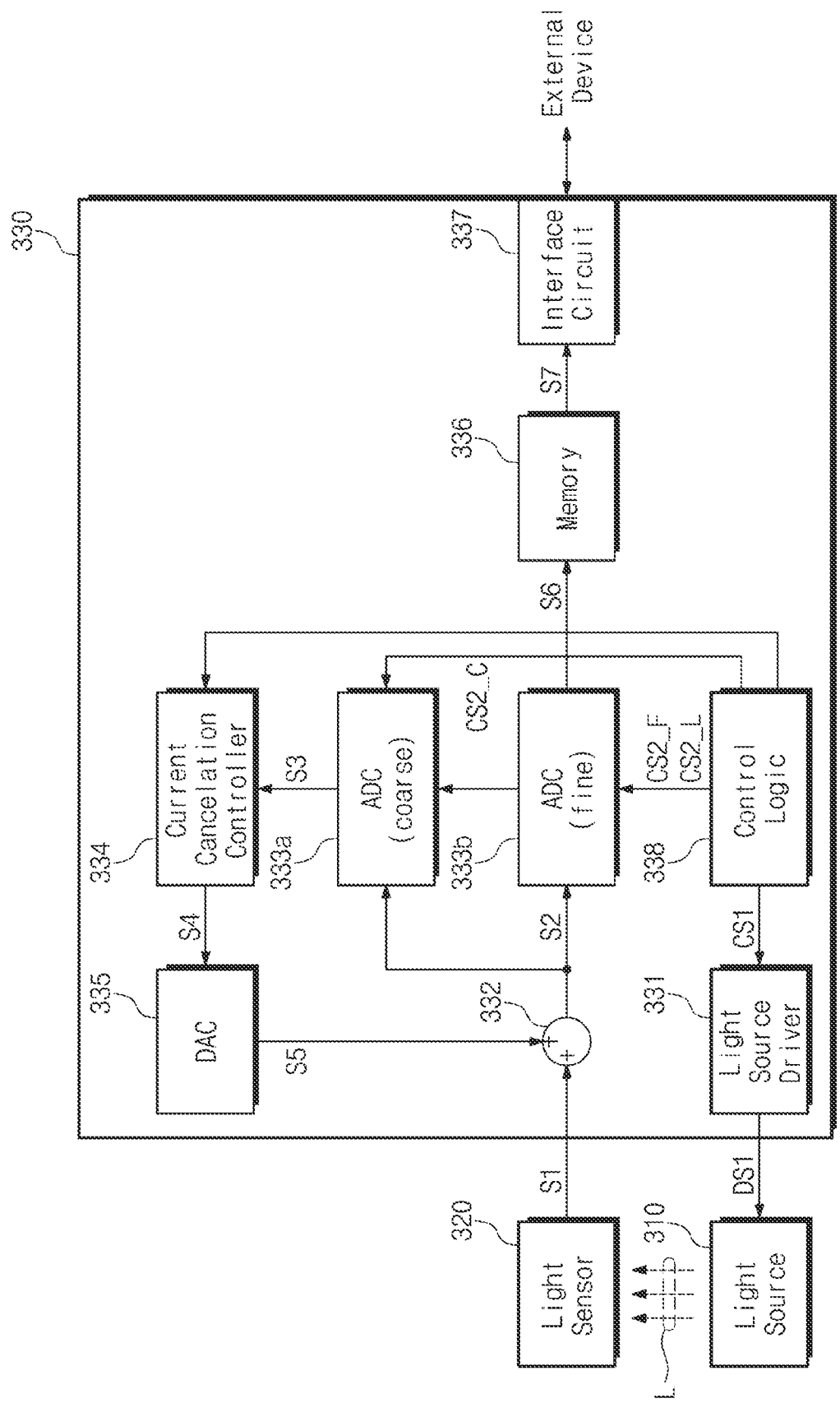
FIG. 10 illustrates an electronic device according to an exemplary embodiment of the present disclosure.

FIG. 10 illustrates an electronic device 300 according to an exemplary embodiment of the present disclosure. Referring to FIG. 10, the electronic device 300 includes a light source 310, a light sensor 320, and a controller 330.

Configurations and operations of the light source 310 and the light sensor 320 may be the same as those of the light source 110 and the light sensor 120 of FIG. 1. Thus, additional description associated with the light source 310 and the light sensor 320 will be omitted to avoid redundancy.

The controller 330 includes a light source driver 331, a subtractor 332, a first analog-to-digital converter 333a, a second analog-to-digital converter 333b, a current cancellation controller 334, a digital-to-analog converter 335, a memory 336, an interface circuit 337, and control logic 338.

The light source driver 331 generates the first driving signal DS1 in response to the first control signal CS1 received from the control logic 338. The light source driver 331 may turn on or turn off the light source 310 based on the first driving signal DS1.

The subtractor 332 is configured to subtract a fifth signal (e.g., a current or a current amount) transferred from the digital-to-analog converter 335 from the first signal S1 (e.g., a current or a current amount) received from the light source 310. The subtractor 332 may output a result of the subtraction as the second signal S2 (e.g., a current or a current amount). For example, the subtractor 332 may be implemented in the form of a wire connection that does not require a separate circuit.

The first analog-to-digital converter (ADC) 333a receives the second signal S2 from the subtractor 332. The first ADC 333a may operate in response to the second coarse control signal CS2_C received from the control logic 338. For example, the first ADC 333a may operate in the coarse mode. In the coarse mode, the first ADC 333a may convert the second signal S2 into a first digital value and may output the first digital value as the third signal S3. For example, the third signal S3 may be a 10-bit signal.

The second analog-to-digital converter (ADC) 333b receives the second signal S2 from the subtractor 332. The second ADC 333b may operate in response to the second fine control signal CS2_F and the second target light sensing control signal CS2_L received from the control logic 338. For example, the second ADC 333b may operate in the fine mode. In the fine mode, the second ADC 333b may convert the second signal S2 into a second digital value or a third digital value and may output the second digital value or the third digital value as the sixth signal S6. For example, the sixth signal S6 may be a 24-bit signal.

In an embodiment, the first ADC 333a may be implemented to include the internal ADC 230 of the ADC 200 of FIG. 4, in more detail, a j-bit ADC. In an embodiment, the second ADC 333b may include the internal subtractor 210, the loop filter 220, the internal ADC 230, in more detail, an i-bit ADC, the logic 240, and the internal DAC 250 of the ADC 200 of FIG. 4.

Except that the current cancellation controller 334 receives the third signal S3 from the first ADC 333a, a configuration and an operation of the current cancellation controller 334 may be the same as those of the current cancellation controller 134 of FIG. 1. Thus, additional description will be omitted to avoid redundancy. A configuration and an operation of the DAC 335 may be the same as those of the DAC 135 to FIG. 1. Thus, additional description will be omitted to avoid redundancy.

Except that the memory 336 receives the sixth signal S6 from the second ADC 333b, a configuration and an operation of the memory 336 may be the same as those of the memory 136 of FIG. 1. Thus, additional description will be omitted to avoid redundancy. A configuration and an operation of the interface circuit 337 may be the same as those of the interface circuit 137 described with reference to FIG. 1. Thus, additional description will be omitted to avoid redundancy.

A configuration and an operation of the control logic 338 may be the same as those of the control logic 138 of FIG. 1 except for the following: the control logic 338 transmits the second coarse control signal CS2_C included in the second control signal CS2 to the first ADC 333a and transmits the second fine control signal CS2_F and the second target light sensing control signal CS2_L included in the second control signal CS2 to the second ADC 333b. Thus, additional description will be omitted to avoid redundancy.

Figure 11:
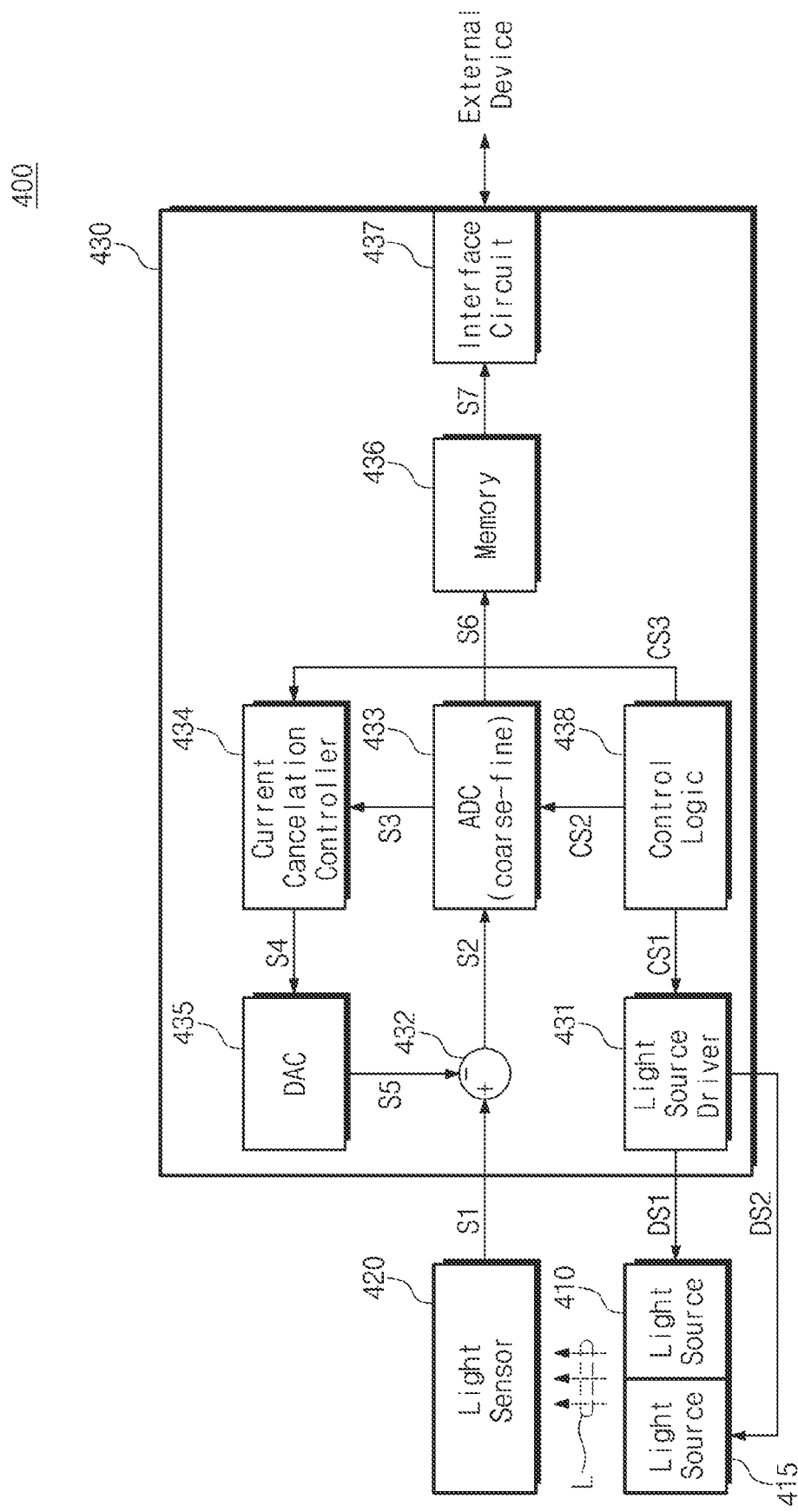
FIG. 11 illustrates an electronic device according to an exemplary embodiment of the present disclosure.

FIG. 11 illustrates an electronic device 400 according to an exemplary embodiment of the present disclosure. Referring to FIG. 11, the electronic device 400 includes a first light source 410, a second light source 415, a light sensor 420, and a controller 430.

The first light source 410 is controlled by the first driving signal DS1 of the controller 430. The first light source 410 may emit the light "L" during a time period that is controlled by the first driving signal DS1. The second light source 415 is controlled by a second driving signal DS2 of the controller 430. The second light source 415 may emit the light "L" during a time period that is controlled by the second driving signal DS2. For example, each of the first light source 410 and the second light source 415 may include a light-emitting diode (LED).

A configuration and an operation of the light sensor 420 may be the same as those of the light sensor 120 described with reference to FIG. 1. Thus, additional description will be omitted to avoid redundancy.

A configuration and an operation of the controller 430 may be the same as those of the controller 130 of FIG. 1 except that the controller 430 controls the first light source 410 by using the first driving signal DS1 and controls the second light source 415 by using the second driving signal DS2. Thus, additional description will be omitted to avoid redundancy.

In each period, the electronic device 400 may be configured to sense a target light by using at least one of the first light source 410 and the second light source 415. When a target light is sensed by using two or more light sources, the controller 430 may output an average or a sum of sensing results to the external device.

In an embodiment, the number of light sources included in the electronic device 400 is not limited. Also, the electronic device 400 may be configured to adaptively adjust the number of light sources that will be activated to sense a target light in each period.

Figure 12:
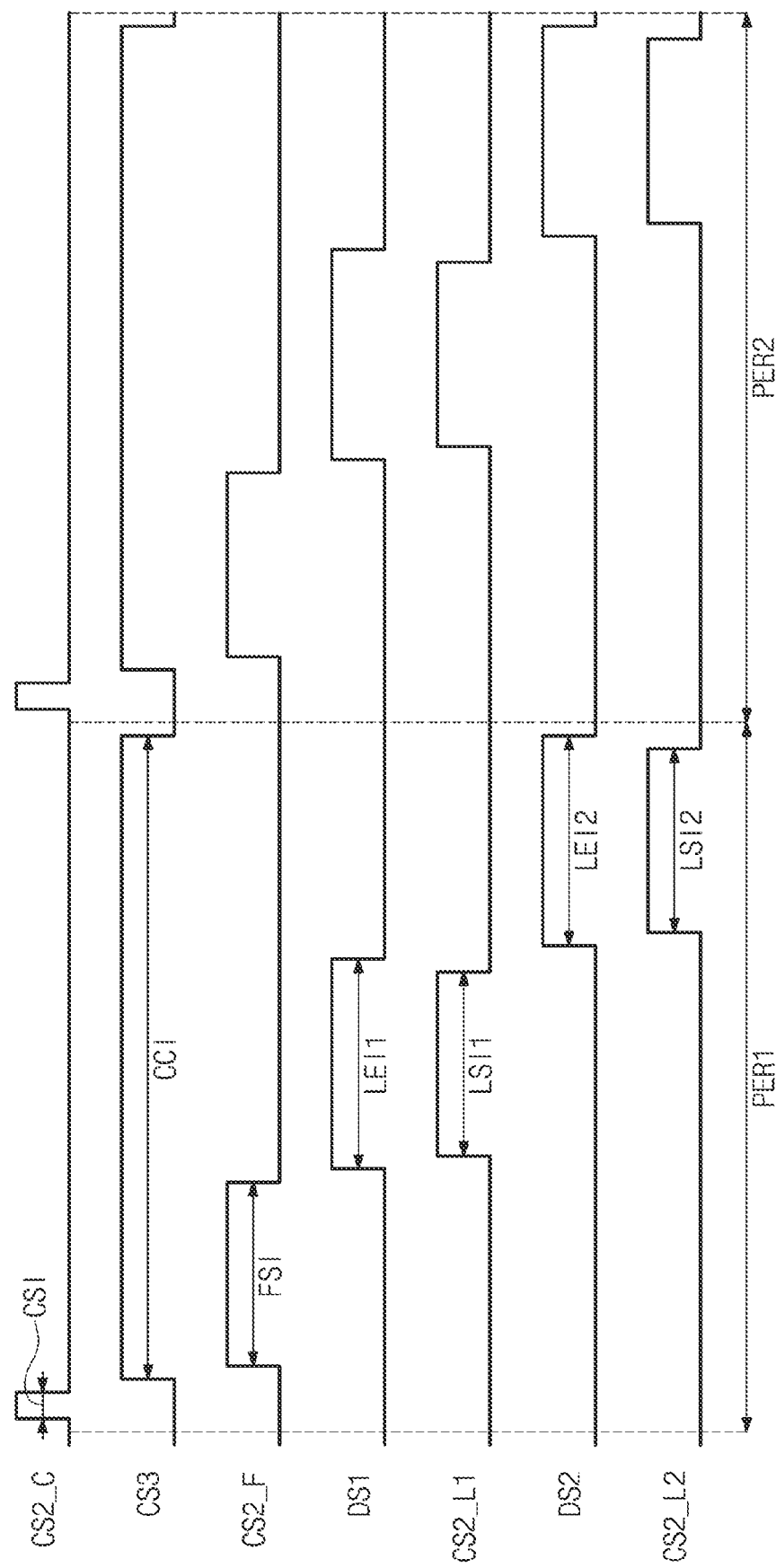
FIG. 12 illustrates an example of waveforms of signals when a controller senses a fine ambient light at least twice.

FIG. 12 illustrates an example of waveforms of signals when the controller 430 senses a fine ambient light at least twice. Referring to FIGS. 1 and 12, each of the first period PER1 and the second period PER2 may include a first time interval, a second time interval, a third time interval, and a fourth time interval.

As described with reference to FIG. 3, the first time interval may include the coarse sensing interval CSI. Based on a first digital value sensed in the coarse sensing interval CSI, the controller 430 maintains the current cancellation interval CCI during the second time interval, the third time interval, and the fourth time interval.

As in the above description given with reference to FIG. 3, the second time interval may include the fine sensing interval FSI. An ADC 433 may store a second digital value converted from the second signal S2 during the fine sensing interval FSI in a memory 436.

As in the above description given with reference to FIG. 3, the third time interval may include a first light-emitting interval LEI1 and a first target light sensing interval LSI1. The ADC 433 may store a third digital value converted from the second signal S2 during the first target light sensing interval LSI1 in the memory 436.

The fourth time interval may include a second light-emitting interval LEI2 and a second target light sensing interval LSI2. The ADC 433 may store a fourth digital value converted from the second signal S2 during the second target light sensing interval LSI2 in the memory 436.

In each period, the memory 436 may calculate an average or a sum of the third digital value sensed in the first target light sensing interval LSI1 and the fourth digital value sensed in the second target light sensing interval LSI2 as a value of a target light. In an embodiment, logic that calculates an average of the second digital value and the fourth digital value stored in the memory 436 may be included in control logic 438 or in the controller 430 as a component coupled such that communication with the memory 436 is possible. For example, the controller 430 or more specifically the control logic 438 may calculate the average of the sum.

An operation according to waveforms of signals of FIG. 12 is the same as the operation according to the waveforms of the signals of FIG. 3 except that an average (or sum) value of the third digital value and the fourth digital value is used as a digital value of a fine ambient light. Thus, additional description will be omitted to avoid redundancy.

In an embodiment, when the average of the third digital value and the fourth digital value is used as a value of a target light, the memory 436 may output a difference between the value of the target light and the second digital value of the fine ambient light. When the sum of the third digital value and the fourth digital value is used as a value of a target light, the memory 436 may output a difference between a value of the target light and twice the second digital value of the fine ambient light.

In an embodiment, as described with reference to FIG. 6, a fine sensing interval may be performed twice or more in each period. As described with reference to FIGS. 8 and 9, at least one of the first digital value and the second digital value may be reused in a next period.

Figure 13:
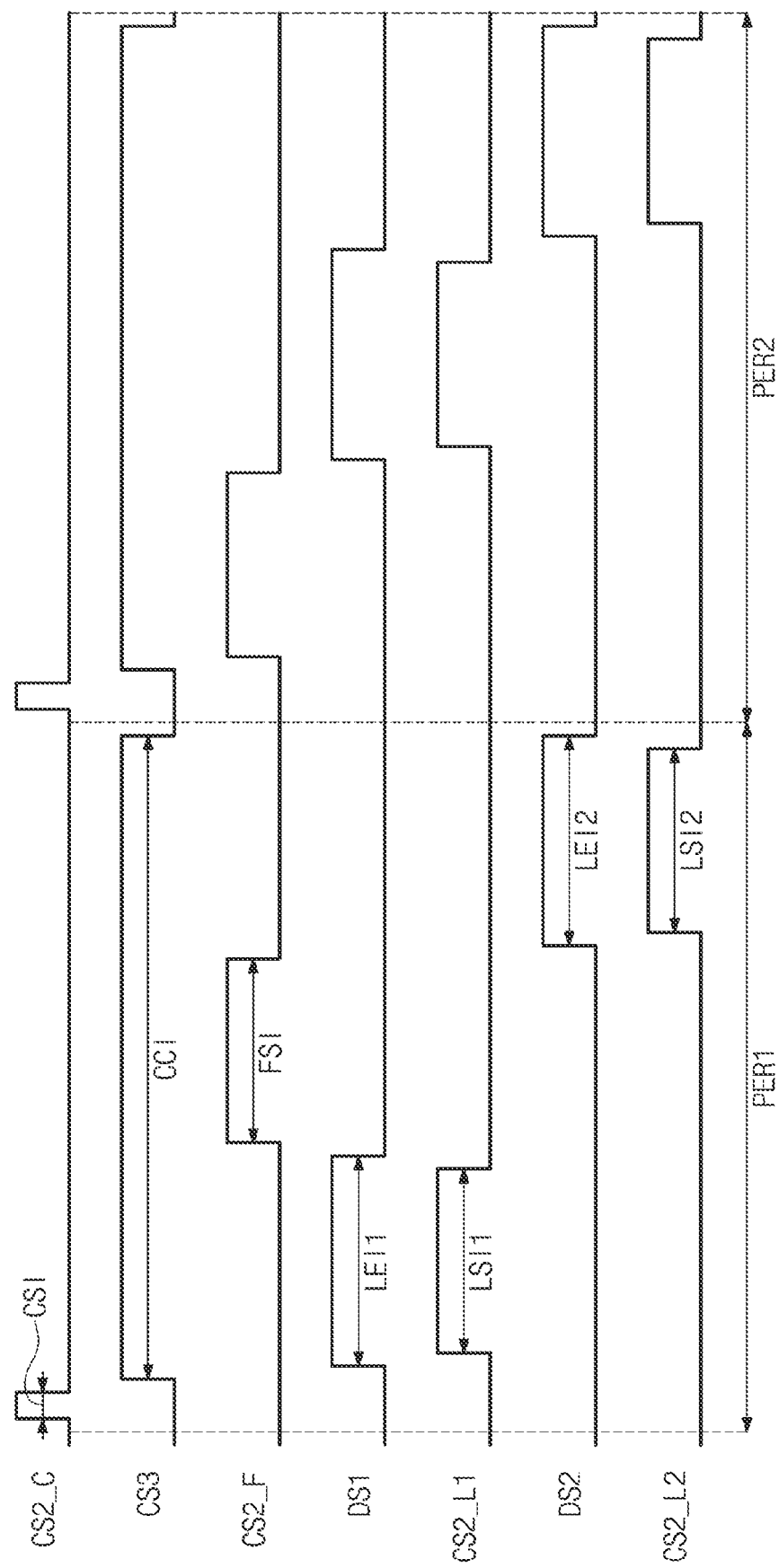
FIG. 13 illustrates another example of waveforms of signals when a controller senses a fine ambient light at least twice.

FIG. 13 illustrates another example of waveforms of signals when the controller 430 senses a fine ambient light at least twice. Compared with FIG. 12, in FIG. 13, the fine sensing interval FSI may be performed between the first target light sensing interval LSI1 and the second target light sensing interval LSI2.

In an embodiment, as described with reference to FIG. 6, a fine sensing interval may be performed twice or more in each period. As described with reference to FIGS. 8 and 9, at least one of a first digital value and a second digital value may be reused in a next period.

In an embodiment, the description is described with reference to FIGS. 12 and 13 as the controller 430 sequentially turns on the first light source 410 and the second light source 415 so as to have target light sensing periods distinguished from each other. However, the controller 430 may be implemented to simultaneously turn on two or more light sources during one target light sensing interval.

Figure 14:
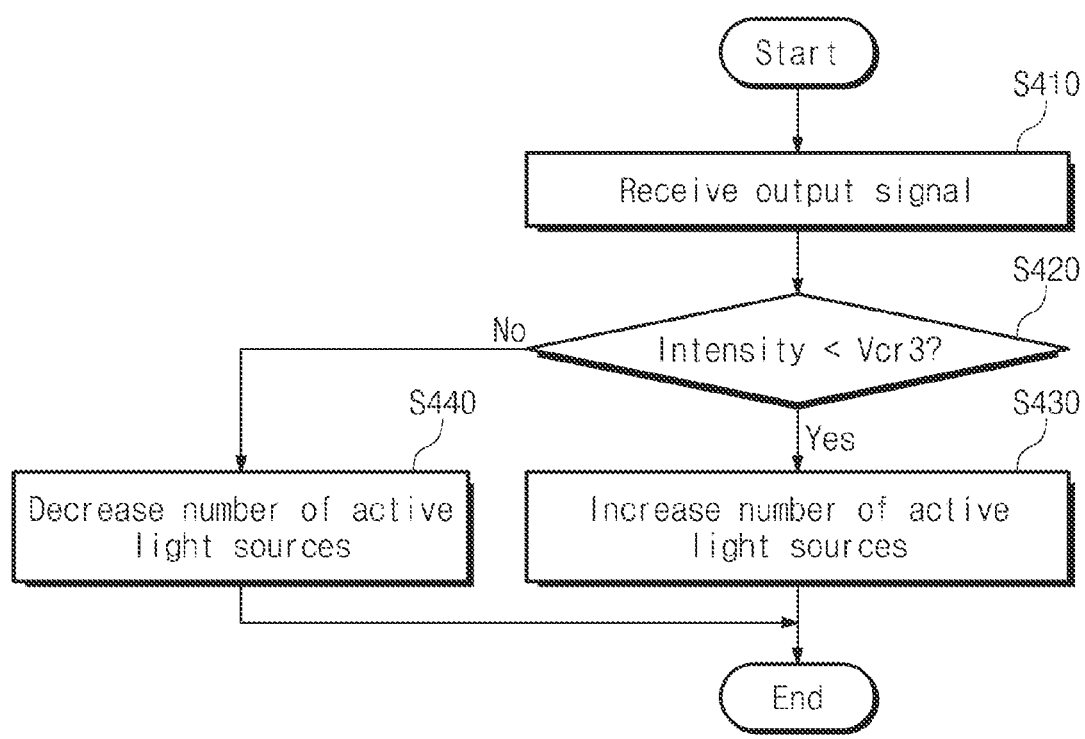
FIG. 14 illustrates an example of a method in which an electronic device adaptively adjusts the number of active light sources.

FIG. 14 illustrates an example of a method for adaptively adjusting the number of light sources that the electronic device 400 activates according to an exemplary embodiment. Referring to FIGS. 11 and 14, in operation S410, the electronic device 100 may receive an output signal. For example, the control logic 438 of the controller 430 may receive an output signal included in the seventh signal S7 from the memory 436. For example, the output signal may be a difference between a digital value of a target light and a digital value of a fine ambient light. The difference may be determined by subtracting the digital value of the fine ambient light from the digital value of a target light to generate a result and calculating a magnitude or absolute value of the result.

In operation S420, the electronic device 400 determines whether the intensity of the output signal is smaller than a third critical value Vcr3. When the intensity of the output signal is smaller than the third critical value Vcr3, in operation S430, the electronic device 400 increases the number of active light sources. An active light source may be a light source that is turned on by the controller 430 to emit the light "L". When the intensity of the output signal is not smaller than the third critical value Vcr3, in operation S440, the controller 430 decreases the number of active light sources. In an embodiment, if the number of active light sources has been decreased to one, and the intensity of the output signal is again not smaller than the third critical value Vcr3, then the number of active lights sources is maintained at one. Further, decreasing the number of active light sources may be performed by turning off one of the light sources.

Figure 15:
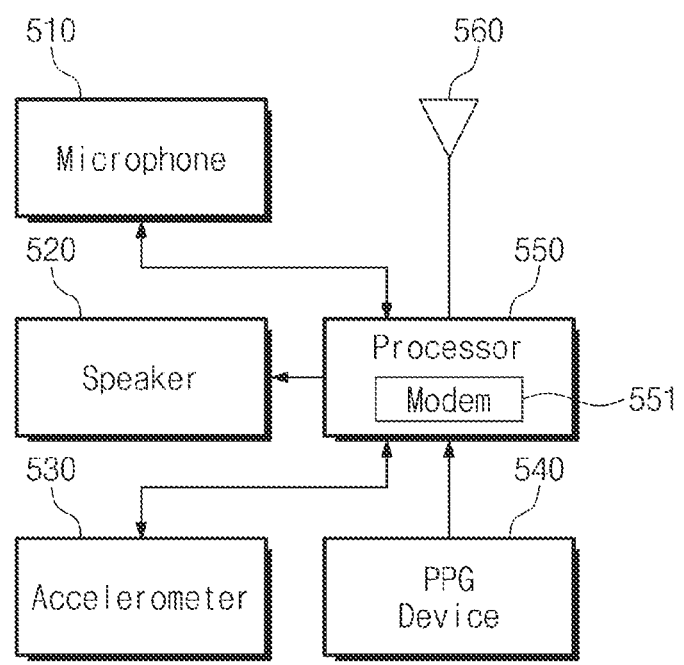
FIG. 15 illustrates an electronic device according to an exemplary embodiment of the present disclosure.

FIG. 15 illustrates an electronic device 500 according to an embodiment of the present disclosure. Referring to FIG. 15, the electronic device 500 includes a microphone 510, a speaker 520, an accelerometer 530, a photoplethysmography (PPG) device 540, a processor 550, and an antenna 560. The microphone 510 may convert an external sound into an electrical signal and may provide the electrical signal to the processor 550.

The speaker 520 may convert an electrical signal provided from the processor 550 into a sound. The accelerometer 530 may sense a change of an acceleration and may provide a sensing result to the processor 550. The PPG device 540 may measure the photoplethysmography of the user. The PPG device 540 may include at least one of the electronic devices 100, 300, and 400 described with reference to FIGS. 1 to 14.

The processor 550 may control the microphone 510, the speaker 520, the accelerometer 530, the PPG device 540, and the antenna 560. The processor 550 may include a modem 551. The processor 550 may communicate with the external device through the antenna 560 by using the modem 551. In an embodiment, the electronic device 500 may be implemented as a wireless earphone or a wireless headset.

The PPG device 540 may be provided to be in contact with the user's body, for example, a part of the user's body or skin adjacent to blood vessels. The PPG device 540 may cancel an ambient light, based on the coarse mode and the fine mode. Accordingly, the accuracy of photoplethysmography that the electronic device 500 provides may be improved.

Figure 16:
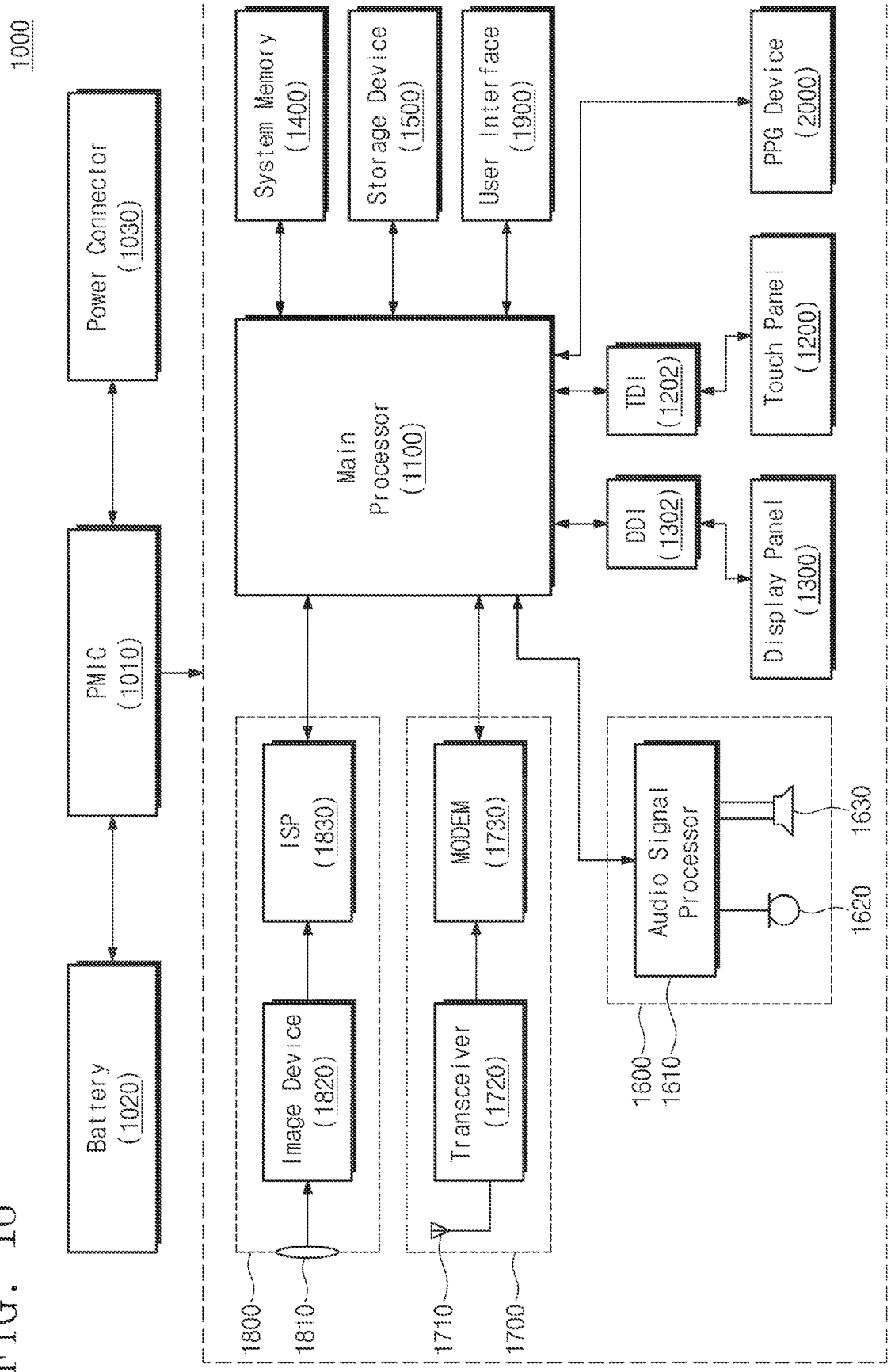
FIG. 16 illustrates an example of an electronic device according to a fifth embodiment of the present disclosure.

FIG. 16 illustrates an example of an electronic device 1000 according to an embodiment of the present disclosure. Referring to FIG. 16, the electronic device 1000 includes a main processor 1100, a touch panel 1200, a touch driver integrated circuit (TDI) 1202, a display panel 1300, a display driver integrated circuit (DDI) 1302, a system memory 1400, a storage device 1500, an audio processor 1600, a communication block 1700, an image processor 1800, and a user interface 1900. In an embodiment, the electronic device 1000 may be one of various electronic devices such as a personal computer, a laptop computer, a server, a workstation, a portable communication terminal, a personal digital assistant (PDA), a portable media player (PMP), a digital camera, a smartphone, a tablet computer, and a wearable device.

The main processor 1100 may control overall operations of the electronic device 1000. The main processor 1100 may control/manage operations of the components of the electronic device 1000. The main processor 1100 may process various operations for the purpose of operating the electronic device 1000. The touch panel 1200 may be configured to sense a touch input from a user under control of the touch driver integrated circuit 1202. The display panel 1300 may be configured to display image information under control of the display driver integrated circuit 1302.

The system memory 1400 may store data that are used in an operation of the electronic device 1000. For example, the system memory 1400 may include a volatile memory such as a static random access memory (SRAM), a dynamic RAM (DRAM), or a synchronous DRAM (SDRAM), and/or a nonvolatile memory such as a phase-change RAM (PRAM), a magneto-resistive RAM (MRAM), a resistive RAM (ReRAM), or a ferroelectric RAM (FRAM).

The storage device 1500 may store data regardless of whether a power is supplied. For example, the storage device 1500 may include at least one of various nonvolatile memories such as a flash memory, a PRAM, an MRAM, a ReRAM, and a FRAM. For example, the storage device 1500 may include an embedded memory and/or a removable memory of the electronic device 1000.

The audio processor 1600 may process an audio signal by using an audio signal processor 1610. The audio processor 1600 may receive an audio input through a microphone 1620 or may provide an audio output through a speaker 1630. The communication block 1700 may exchange signals with an external device/system through an antenna 1710. A transceiver 1720 and a modulator/demodulator (MODEM) 1730 of the communication block 1700 may process signals exchanged with the external device/system, based on at least one of various wireless communication protocols: long term evolution (LTE), worldwide interoperability for microwave access (WiMax), global system for mobile communication (GSM), code division multiple access (CDMA), Bluetooth, near field communication (NFC), wireless fidelity (Wi-Fi), and radio frequency identification (RFID).

The image processor 1800 may receive a light through a lens 1810. An image device 1820 and an image signal processor (ISP) 1830 included in the image processor 1800 may generate image information about an external object, based on a received light. The user interface 1900 may include an interface capable of exchanging information with a user, except for the touch panel 1200, the display panel 1300, the audio processor 1600, and the image processor 1800. The user interface 1900 may include a keyboard, a mouse, a printer, a projector, various sensors, a human body communication device, etc.

The electronic device 1000 may further include a power management IC (PMIC) 1010, a battery 1020, and a power connector 1030. The power management IC 1010 may generate an internal power from a power supplied from the battery 1020 or a power supplied from the power connector 1030, and may provide the internal power to the main processor 1100, the touch panel 1200, the touch driver integrated circuit (TDI) 1202, the display panel 1300, the display driver integrated circuit (DDI) 1302, the system memory 1400, the storage device 1500, the audio processor 1600, the communication block 1700, the image processor 1800, and the user interface 1900.

The electronic device 1000 may further include a PPG device 2000 (e.g., 540). The PPG device 2000 may measure the photoplethysmography of the user. The PPG device 2000 may include at least one of the electronic devices 100, 300, and 400 described with reference to FIGS. 1 to 14.

The PPG device 2000 may be provided to be in contact with the user's body, for example, a part of the user's body or skin adjacent to blood vessels. The PPG device 2000 may cancel an ambient light, based on the coarse mode and the fine mode. Accordingly, the accuracy of photoplethysmography that the electronic device 1000 provides may be improved.

Alternatively, the electronic device 1000 may be implemented with various mobile devices such as a smartphone or a smart pad. Also, the electronic device 1000 may be implemented with various wearable devices such as a smart watch, smart glasses, and an augmented reality goggles.

According to an exemplary embodiment, a mobile device for performing photoplethysmography includes a light source (e.g., 110), a light sensor (e.g., 120), an ADC (e.g., 133), and a controller (e.g., 130).

The controller is configured to turn off the light source, control the light sensor to output a first signal representing first ambient light, and control the ADC to convert the first signal into a second signal having a first number of bits (e.g., representing coarse ambient light). For example, referring to FIG. 1, S2 output from the subtractor 132 during a second period could be the first signal since no canceling takes place during the second period. For example, S5 output from the DAC 135 during a third period as a result of the ADC 133 processing the first signal in a coarse mode is an example of the second signal.

The controller is further configured to control the light sensor to output a third signal representing second ambient light, subtract the second signal from the third signal to generate a fourth signal, and control the ADC to convert the fourth signal into a fifth signal having a second number of bits greater than the first number (e.g., representing fine ambient light). For example, S1 output from the light sensor 120 during a fourth period is an example of the third signal, S2 output from the subtractor 132 during a fifth period is an example of the fourth signal, and S5 (e.g., representing an amount of fine ambient light) output from the DAC 135 during a sixth period as a result of the ADC 133 processing S2 in a fine mode may be an example of the fifth signal.

The controller is additionally configured to configured turn on the light source, control the light sensor to output a sixth signal representing a target light, and subtract the fifth signal from the sixth signal to generate a photoplethysmography signal. The ADC may generate the third signal while operating in a coarse mode and may generate the fifth signal while operating in a fine mode. For example, S1 output from the subtractor 132 during a seventh period while the light source 110 is turned on may be an example of the target light, and S2 output from the subtractor 131 during an eight period may be an example of the photoplethysmography signal.

In the above embodiments, some components according to embodiments of the present disclosure are described by using blocks. The blocks may be implemented with various hardware devices, such as an integrated circuit, an application specific IC (ASIC), a field programmable gate array (FPGA), and a complex programmable logic device (CPLD), firmware driven in hardware devices, software such as an application, or a combination of a hardware device and software. Also, the blocks may include circuits implemented with semiconductor elements in an integrated circuit or circuits enrolled as intellectual property (IP).

According to the present disclosure, an ambient light may be canceled through a coarse mode and a fine mode. Because the ambient light is canceled more quickly or more accurately, an electronic device performing photoplethysmography at an improved speed and with improved accuracy and an operating method of the electronic device are provided.

While the present disclosure has been described with reference to embodiments thereof, it will be apparent to those of ordinary skill in the art that various changes and modifications may be made thereto without departing from the spirit and scope of the present disclosure as set forth in the following claims.

What is claimed is:

1. An electronic device comprising:
a light source;
a light sensor; and
a controller configured to sense a coarse amount of ambient light by turning off the light source and performing sensing in a coarse mode by operating an analog-to-digital converter at a first resolution on data based on a first output from the light sensor and to sense a fine amount of the ambient light by performing sensing in a fine mode by operating the analog-to-digital converter at a second higher resolution on data based on a second output from the light sensor,
wherein the controller is configured to:
sense an amount of a target light by turning on the light source and performing sensing by using the light sensor while the light source emits a light; and
output information based on the coarse amount of the ambient light, the fine amount of the ambient light, and the amount of the target light.

2. The electronic device of claim 1, wherein, during sensing the fine amount of the ambient light and during sensing the amount of the target light, the controller is configured to cancel an amount, which corresponds to the coarse amount of the ambient light, from an amount of a current output from the light sensor.

3. The electronic device of claim 1, wherein the controller outputs a value corresponding to an amount obtained by subtracting the coarse amount of the ambient light from the amount of the target light, as the information.

4. The electronic device of claim 1, wherein the light source includes a light-emitting diode,
wherein the light sensor includes a photodiode, and
wherein the information includes a photoplethysmography signal.

5. The electronic device of claim 1, wherein the analog-to-digital converter is configured to:
convert the coarse amount of the ambient light into a first digital value in a first mode;
convert the fine amount of the ambient light into a second digital value in a second mode; and
convert the amount of the target light into a third digital value in the second mode.

6. The electronic device of claim 5, wherein, in the first mode, the analog-to-digital converter operates as a successive approximation (SAR) analog-to-digital converter, and
wherein, in the second mode, the analog-to-digital converter operates as a delta-sigma analog-to-digital converter.

7. The electronic device of claim 5, wherein the analog-to-digital converter comprises:
a loop filter;
an internal analog-to-digital converter configured to convert an output signal of the loop filter into "j" bits in the first mode and to convert the output signal of the loop filter into "i" bits in the second mode;
a digital-to-analog converter configured to convert the "i" bits into a current in the second mode;
a subtractor configured to subtract the current output from the digital-to-analog converter from an input signal of the analog-to-digital converter so as to be provided to the loop filter; and
a logic circuit configured to perform filtering on the "i" bits and to output a result of the filtering in the second mode,
wherein the "i" is a positive integer greater than "0", and
wherein the "j" is a positive integer greater than the "i".

8. The electronic device of claim 7, wherein, in the first mode, the analog-to-digital converter outputs the "j" bits as the first digital value, and wherein, in the second mode, the analog-to-digital converter outputs the "i" bits as the second digital value or the third digital value.

9. The electronic device of claim 5, wherein the controller comprises:

a digital-to-analog converter configured to output a current corresponding to the first digital value in the second mode;

a subtractor configured to subtract the current output from the digital-to-analog converter from a current received from the light sensor in the second mode so as to be provided to the analog-to-digital converter;

a memory configured to store the second digital value and the third digital value in the second mode; and an interface circuit configured to output a difference between the third digital value and the second digital value.

10. The electronic device of claim 1, wherein the analog-to-digital converter comprises:

a first analog-to-digital converter configured to convert the coarse amount of the ambient light into a first digital value; and a second analog-to-digital converter configured to convert the fine amount of the ambient light into a second digital value and to convert the amount of the target light into a third digital value.

11. An operating method of an electronic device which includes a light source and a light sensor, the method comprising:

sensing a first current amount by turning off the light source and operating an analog-to-digital converter (ADC) at a first resolution on data based on a first output from the light sensor, during a first time interval;

sensing a second current amount by operating the ADC at a second higher resolution on data based on a second output from the light sensor and the first current amount, during the second time interval; and during a third time interval, emitting a light by turning on the light source and sensing a third current amount by using the light sensor and the second current.

12. The method of claim 11, further comprising:

outputting a difference between the third current amount and the second current amount.

13. The method of claim 11, further comprising:

canceling a current corresponding to the first current amount from an output of the light sensor during a fourth time interval;

sensing a fourth current amount by using the light sensor during the fourth time interval; and outputting a difference between the third current amount and an average of the second current amount and the fourth current amount.

14. The method of claim 11, further comprising:

sensing a fourth current amount by using the light sensor during a fourth time interval;

canceling a current corresponding to the fourth current amount from an output of the light sensor during a fifth time interval; and during the fifth time interval, emitting a light by using the light source and sensing a fifth current amount by using the light sensor.

15. The method of claim 11, further comprising:

canceling a current corresponding to the first current amount from an output of the light sensor during a fourth time interval and a fifth time interval;

sensing a fourth current amount by using the light sensor during the fourth time interval; and during the fifth time interval, emitting a light by using the light source and sensing a fifth current amount by using the light sensor.

16. The method of claim 11, further comprising:

canceling a current corresponding to the first current amount from an output of the light sensor during a fourth time interval; and during the fourth time interval, emitting a light by using the light source and sensing a fourth current amount by using the light sensor.

17. The method of claim 11, wherein the light source includes two or more light sources, and wherein the method further comprises:

adjusting a number of active light sources from among the two or more light sources, based on a difference of the third current amount and the second current amount.

18. The method of claim 11, wherein the light source is a first light source, and wherein the electronic device further includes a second light source, and wherein the method further comprises:

canceling a current corresponding to the first current amount from an output of the light sensor during a fourth time interval; and during the fourth time interval, emitting a light by using the second light source and sensing a fourth current amount by using the light sensor.

19. An electronic device comprising:

a photoplethysmography device configured to output a photoplethysmography signal; and a processor configured to receive the photoplethysmography signal from the photoplethysmography device and to communicate the photoplethysmography signal to an external device, wherein the photoplethysmography device comprises:

a light source;

a light sensor; and a controller configured to perform sensing by turning off the light source and operating an analog-to-digital converter (ADC) at a first resolution on data based on a first output from the light sensor to sense a coarse amount of ambient light, in a coarse mode, wherein the controller is configured to:

sense a fine amount of the ambient light by performing sensing by operating the ADC at a second higher resolution on data based on a second output from the light sensor in a fine mode and the first output; and sense an amount of a target light by performing sensing by turning on the light source and using the light sensor while the light source emits a light and the second output.

20. The electronic device of claim 19, wherein the ADC operates in a successive approximation (SAR) manner while sensing the coarse amount of the ambient light and operates in a delta-sigma manner while sensing the fine amount of the ambient light and sensing the amount of the target light.

* * * * *